United States Patent [19]

Heady

[11] 4,276,379

[45] Jun. 30, 1981

[54] PREPARATION OF HIGH FRUCTOSE SYRUPS FROM SUCROSE

[75] Inventor: Robert E. Heady, Argo, Ill.

[73] Assignee: CPC International Inc., Englewood Cliffs, N.J.

[21] Appl. No.: 913,278

[22] Filed: Jun. 9, 1978

Related U.S. Application Data

[63] Continuation-in-part of Ser. No. 807,289, Jun. 16, 1977, abandoned.

[51] Int. Cl.$^3$ .................. C12P 19/24; C12P 19/18; C12P 19/04; C12N 9/10
[52] U.S. Cl. ........................................ 435/94; 435/97; 435/101; 435/193; 435/111
[58] Field of Search ............... 195/4, 7, 11, 31 R, 195/31 P, 31 F, 62, 65, 66 R; 435/94, 99, 97, 101, 193, 911

[56] References Cited

U.S. PATENT DOCUMENTS

| 2,729,587 | 1/1956 | Koepsell et al. | 435/97 |
| 3,050,444 | 8/1962 | Holstein et al. | 435/94 |
| 3,184,334 | 5/1965 | Sargent | 127/46 R |
| 3,720,583 | 3/1973 | Fisher | 195/31 R |
| 3,812,010 | 5/1974 | Nitsch | 435/94 |
| 3,817,832 | 6/1974 | Lloyd et al. | 195/31 R |
| 3,834,940 | 9/1974 | Khaleeluddin et al. | 127/46 A |
| 3,935,070 | 1/1976 | Suekane et al. | 195/31 R |

FOREIGN PATENT DOCUMENTS

| 24763 | 2/1965 | German Democratic Rep. |
| 43-19839 | 8/1968 | Japan . |
| 49-101593 | 9/1974 | Japan . |
| 51-73140 | 6/1976 | Japan . |
| 51-73141 | 6/1976 | Japan . |
| 402539 | 9/1973 | U.S.S.R. . |
| 464616 | 3/1975 | U.S.S.R. . |

OTHER PUBLICATIONS

Singh et al., *Phytochem.*, vol. 10, (1971), pp. 2037–2039.
Loitsyanskaya, et al., *Mikrobiologiya*, vol. 40, No. 3, (1971), pp. 505–508.
Kawai et al., "Polyfructan and Oligofructans Synthesized from Sucrose by Conidia of *Aspergillus sydowi*, IAM 2544," *Agr. Biol. Chem.*, vol. 37, No. 9, (1973), p. 2111–2119.
Krichevsky et al., *J. Dent. Res.*, vol. 48, (1969), pp. 938–942.
Binkley et al., *Carbohyd. Res.*, vol. 10, (1969), pp. 245–258.
Pigman et al., *The Carbohydrates*, vol. II A, 2nd ed., Academic Press, New York, (1970), pp. 274–281, 335, 336.
Abdou, *Phytopathol. Z.*, vol. 66, No. 2, (1969), pp. 147–167.
Guthof, *Zbl. Bakt. I. Abt. Orig.*, vol. 215, (1970), pp. 435–440.
Barman, *Enzyme Handbook*, vol. I, Springer-Verlag, Inc., New York, (1969), p. 310.
Whiting et al., *J. Inst. Brew.*, vol. 73, (1967), pp. 442–445.
Newbrun et al., *Carbohyd. Res.*, vol. 6, (1968), pp. 165–170.
Albon et al., "Ketose: A Trisaccharide Formed From Sucrose by Yeast Ivertase", *J. Chem. Soc.*, (1953), pp. 24–27.
*Rodd's Chemistry of Carbon Compounds*, (1967), Elseurer Pub. Co., N.Y., pp. 687–688.
Komoto et al., *Seito Gijutsu Kenkyukaishi*, vol. 20, (1968), pp. 29–38.
Kopeloff et al., *J. Agr. Res.*, vol.18, (1919), pp. 195–209.
Reese, *Biochem. Biophys. Acta*, vol. 13, No. 1, (1966), pp. 79–83.
Rapoport et al., *Bull. Soc. Chem. Biol.*, vol. 48, (1966), pp. 1311–1322.
Kopeloff et al., *J. Biol. Chem.*, vol. 43, (1920), pp; 171–187.
Lewis et al., *Carbohyd. Res.*, vol. 5, (1967), pp. 194–201.
Howell et al., *Arch. Oral Biol.*, vol. 12, No. 4, (1967), pp. 571–573.
Hestrin et al., *Biol. Chem. J.*, vol. 37, (1943), pp. 450–456.
Ebert et al., *Z. Naturforschg.*, vol. 19b, (1964), pp. 23–28, 211–221, 287–292.
Rapoport et al., *Bull. Soc. Chim. Biol.*, vol. 48, No. 12, (1966), pp. 1323–1348.
Hestrin, et al., *Biochem. J.*, vol. 38, (1944), pp. 2–10.
Avigad et al., *Bull. Res. Counc. Israel*, vol. 11, A(4), (1964), pp. 253–257.
Eisenberg et al., *Bull. Res. Counc. Israel*, Sect. A, Chem. 11(4), (1963), pp. 269–274.
Ohad et al., *Proc. Isreal Chem. Soc.*, vol. 9A, (1960), pp. 91–93.
Dedoner et al., *Bull. Soc. Chim. Biol.*, vol. 45, (1963), pp. 477–491.
Ueda et al., *Appl. Microbiol.*, vol. 11, (1963), pp. 211–215.
Pigman et al., *The Carbohydrates*, Academic Press, N.Y., (1957), pp. 683–684.
Hestrin et al., *Biochem. J.*, vol. 64, (1956), pp. 340–350.
Avigad et al., *Biochem. Biophys. Acta*, vol. 20, (1956), pp. 129–134.
Tanaka et al., *Agr. Biol. Chem.*, vol. 42, No. 2, (1978), pp. 323–326.
Feingold et al., *J. Biochem.*, vol. 224, No. 1, (1957), pp. 295–307.
Loewenberg et al., *Can. J. Micro.*, vol. 3, (1957), pp. 643–650.
Barker, *Process Biochem.*, (1976), pp. 20, 25.
Edelman et al., *Biochem. J.*, vol. 53, (1953), pp. i–iii.
Edelman, *Biochem. J.*, vol. 57, (1954), pp. 22–33.
Whitaker et al., *Arch. Oral Biol.*, vol. 21, No. 10, (1976), pp. 565–570.
Pazur, *J. Biol. Chem.*, vol. 119, (1952), pp. 217–225.
De Whalley, *Int. Suyar J.*, vol. 54, (1952), p. 127.
Bealing, *Biochem. J.*, vol. 55, (1953), pp. 93–101.
Pascal et al., *Carbohyd. Res.*, vol.24, No. 2, (1973), pp. 365–377.
Bacon et al., *J. Chem. Soc.*, (1953), pp. 2528–2530.
Pabst, *Infection and Immunity*, vol. 15, No. 2, (1977), pp. 518–526.

Tomoda et al., "Production of Several Oligosaccharudes from Sucrose by Action of an Aspergillus Enzyme Preparation and Structural Studies of the Products", *Kyoritsu Yakka Daigaku Kenkyu Nempo*, vol. 20, (1975), pp. 1–8.
Komoto et al., Seito Gijutsu Kenkykaishi, vol. 20, (1968), pp. 29–38.
Hankin et al., *Applied Environ. Micro.*, vol. 33, No. 3, (1977), pp. 522–524.
Cooke, "An Ecological Life History of Aureobasidium Pullulans (De Bary) Arnaud", *Myeopath et Mycol. Appl.*, vol. 12, No. 1, (1959), pp. 1,2.
Feingold et al., *Biochem. J.*, vol. 64, (1956), pp. 351–361.
Whitaker et al., *Arch. Oral Biol.*, vol. 21, No. 10, (1976), pp. 565–570.
van der Hoeven et al., *Caries Res.*, vol. 10, (1976), pp. 33–48.
Teppaz-Misson, *Comptes Rendus Hebdomadaires des Seances de l'Academie des Sciences*, Serie D, vol. 280, No. 13, (1975), pp. 1567–1570.
Krauze et al., *Zeszyty Naukewe Akademiz Ekonomiczna w Poznaniu*, vol. 62, (Series 1), (1975), pp. 55–59.
Uchiyama, *Biochim. Biophys. Acta*, vol. 397, (1975), pp. 153–163.
Chassy et al., *Infection and Immunity*, vol. 14, No. 2, (1976), pp. 408–415.
Rosell et al., *Acta Chem. Scand.*, B28 (1974), p. 589.
Takashita, *J. Bact.*, vol. 116, (1973), pp. 503–506.
Baird et al., *J. Dent. Res.*, vol. 52, Supp. to No. 5, Abstr. 101, (1973), pp. 954–955.
Chambert et al., *Eur. J. Biochem.*, vol. 41, No. 2, (1974), pp. 286–300.
Joyeux et al., *Ann. Inst. Pasteur*, vol. 121, (1971), pp. 293–309.
Binkley et al., *Carbohyd. Res.*, vol. 23, (1972), pp. 301–306.
Gibbons, *Caries Res.*, vol. 6, No. 2, (1972), pp. 122–131.
Taguchi et al., *Agr. Biol. Chem.*, vol. 37, No. 7, (1973), pp. 1635–1641.
Carlsson, *Caries Res.*, vol. 4, (1970), pp. 97–113.
Reese et al., *Can. J. Micro.*, vol. 17, (1971), pp. 329–332.

*Primary Examiner*—Thomas G. Wiseman

[57] ABSTRACT

This invention relates generally to (1) processes for the production and isolation of a novel fructosyl transferase enzyme from the fermentation broth of *Pullularia pullulans*, (2) enzymatic transfructosylation of sucrose to produce a novel fructose-polymer containing substrate, and (3) production of fructose syrups containing greater than 55% fructose from said novel substrate.

7 Claims, No Drawings

PREPARATION OF HIGH FRUCTOSE SYRUPS FROM SUCROSE

This application is a continuation in part of application Ser. No. 807,289 filed June 16, 1977, now abandoned.

FIELD OF THE INVENTION

This invention relates generally to enzymatic transfructosylation of sucrose. More particularly, this invention relates to a unique process for the production of fructose from sucrose by way of a fructose polymer-containing substrate. This process provides a novel enzymatic approach for the production of high fructose syrups having a fructose content significantly higher than presently obtainable by glucose isomerization of starch hydrolysates, without the necessity for physical separation of the resultant fructose end-product. This process is particularly adaptable to the production of fructose syrups containing greater than 55% fructose and higher. The invention also provides a novel transfructosylase enzyme from cultures of the yeast *Pullularia pullulans,* found to be useful in such production.

This invention gives rise to a number of products. These include the ultimate fructose or a high fructose syrup, as well as various intermediate products such as the fructose polymer, initial fructose polymer (or polysaccharide) containing substrate, substrate from which the polymer has been removed, and substrate (with or without the polymer) after isomerization. Each of these products is directly useful in its own right.

Each of these productions has the properties of conventional sugars and syrups and may be employed in their customary applications. These include, for example, use as food sweetening agents and as raw materials for the preparation of pharmaceuticals. In addition, these products may be employed in the common industrial applications for sugars and syrups. Thus, they may be used in producing adhesives, humectants, glassine paper, tanning agents, electrical insulators, foundry core binders, insecticides, dyes and the like or more generally as plasticizers, thickening agents, etc. In short, they are useful throughout the broad spectrum of utilities in which analogous products have already been employed.

DEFINITIONS

Because of the many terms that are in common use in the art, the following definitions are provided to define the meaning of these terms as used herein:

Glucose and Dextrose

The terms "glucose" and "dextrose" are employed interchangeably in this application to embrace this monosaccharide in any form in solution or dry.

Sucrose

The term "sucrose" refers to this disaccharide in refined or raw form, in solution or dry, from any sucrose raw material source, e.g. sugar cane or sugar beets. In the practice of this invention the sucrose starting material is typically employed in aqueous medium.

Fructose and Levulose

The terms "fructose" and "levulose" are generally employed interchangeably in the art to refer to the isomer of dextrose that is sweeter than dextrose. Fructose is found in honey and in invert sugar, along with dextrose, and is valuable because of its sweetness. The terms levulose and fructose will be used interchangeably in this specification to refer to this monosaccharide in any form, in solution or dry.

Enzyme Preparation

The term "enzyme preparation" is used herein to refer to any composition of matter that exhibits the desired enzymatic activity. The term is used to refer, for example, to live whole cells, dry cells, cell extracts, refined and concentrated preparations derived from the cells and from culture liquors. The enzyme preparations may be used either as a solution or in an immobilized form in the practice of this invention.

Isomerase Enzyme

Any enzyme preparation that isomerizes dextrose to levulose is referred to herein as an "isomerase enzyme." These enzymes are well known in the art and have been referred to as dextrose isomerase, xylose isomerase and glucose isomerase. Such enzymes can be derived from a variety of suitable microorganisms. Examples of such microorganisms include those of the genera Streptomyces, Bacillus, Arthrobacter, Actinoplanes, Curtobacterium and others. Specific microorganisms which can be used in the preparation of isomerase enzyme include *Streptomyces fradiae, Streptomyces phaeochromogenes, Streptomyces albus* ATCC No. 21,132; *Streptomyces wedmorensis* ATCC No. 21,230 (see U.S. Pat. No. 3,616,221); *Streptomyces rubiginosus* ATCC No. 21,175 and ATCC No. 21,176 (see U.S. Pat. No. 3,666,628 and U.S. Pat. No. 3,788,945); *Streptomyces olivaceus* NRRL 3583 (see U.S. Pat. No. 3,625,828); *Streptomyces olivaceus* NRRL 3916 (see British Pat. No. 1,376,787); *Streptomyces olivochromogenes* ATCC No. 21,114 (see U.S. Pat. No. 3,622,463 and U.S. Pat. No. 3,770,589); *Streptomyces olivochromogenes* ATCC Nos. 21,713, 21,714 and 21,715 (see U.S. Pat. No. 3,622,463 and U.S. Pat. No. 3,813,318); *Streptomyces glaucescens* (see British Pat. No. 1,410,579; *Streptomyces violaceoniger* (see German OS No. 2,417,642); *Arthrobacter nov* sp NRRL B-3742, NRRL B-3725, NRRL B-3726 and NRRL B-3728 (see U.S. Pat. No. 3,645,848; *Bacillus stearothermophilus* ATCC No. 21,365, NRRL B-3680, NRRL B-3681, and NRRL B-3682 (see U.S. Pat. No. 3,826,714); *Lactobacillus brevis; Bacillus coagulans* NRRL Nos. 5649–5666, and particularly NRRL No. 5650 (see German OS No. 2,400,323); *Actinoplanes missouriensis* NRRL B-3342, *Actinoplanes philippinesis* ATCC No. 12,427, *Actinoplanes armeniacus* ATCC No. 15,676 and Actinoplanes sp ATCC 23,342 (see U.S. Pat. No. 3,834,988); *Aerobacter levanicum* NRRL B-1678 (see U.S. Pat. No. 3,813,320); *Nocardia asteroides* ATCC No. 21,943, *Nocardia dassonvillei* ATCC No. 21,944, *Micromonospora coerula* ATCC No. 21,945, *Microbispora rosea* ATCC No. 21,946 and *Microellobospora flavea* ATCC No. 21,947 (see U.S. Pat. No. No. 3,829,362); and Curtobacterium (see Japanese Sho 50/132176 (1975)).

A preferred isomerase enzyme useful in the practice of the present invention is derived from *Streptomyces olivochromogenes* ATCC No. 21,713, ATCC No. 21.714 or ATCC No. 21,715, (the latter of which is a single colony isolate of ATCC No. 21,713) as disclosed in U.S. Pat. No. 3,813,318 and U.S. Application Ser. No. 589,115, filed June 23, 1975, particularly when prepared by the process described in U.S. Pat. No. 3,770,589 or U.S. Pat. No. 3,813,318.

Recently, the art has come to recognize processes where the isomerase enzyme is immobilized on a water-insoluble inert carrier. The immobilized enzyme is then suitable for use in continuously converting glucose to a high fructose syrup. Examples of such processes are described in U.S. Pat. Nos. 3,708,397; 3,788,945; 3,850,751; 3,868,304; Belgium Pat. No. 819,859; and U.S. Patent Application Ser. No. 505,823 (Belgium Pat. No. 810,480).

Isomerase Unit

"Isomerase unit" is defined as the amount of enzyme activity that is required to produce one micromole of levulose per minute under the isomerization conditions described hereafter under the heading "Assay of Isomerase Activity".

Assay of Isomerase Activity

As used herein this term refers to the assay procedure which involves making a spectrophotometric determination of the ketose produced from a glucose solution under a standardized set of conditions.

A stock solution is made up in the following manner:

| STOCK SOLUTION FOR ASSAY | |
|---|---|
| Component | Amount |
| 0.1 M $MgSO_4 \cdot 7H_2O$ | 1 ml |
| 0.001 M $CoCl_2 \cdot 6H_2O$ | 1 ml |
| 1 M sodium phospate buffer, pH 7.5 | 0.5 ml |
| Anhydrous D-glucose | 1.44 g |

Add distilled water to make up a total volume of 7.5 ml

The enzyme preparation to be assayed is first diluted to contain from 1 to 6 isomerase units per ml.

An enzymatic isomerization is conducted by adding 1 ml of the enzyme preparation to 3 ml of the stock solution, and incubating for 30 minutes at 60° C. At the end of the incubation period, a 1 ml aliquot is taken and quenched in a 9 ml volume of 0.5 N perchloric acid. The quenched aliquot is then diluted to a total volume of 250 ml. As a control, for comparative purposes, a glucose blank is also run by substituting 1 ml of water for the 1 ml of the enzyme preparation in solution at the beginning of the incubation period.

The ketose is then determined by a cysteine-sulfuric acid method. For the purposes of this assay, one isomerase unit is defined as the amount of enzyme activity that is required to produce one micromole of levulose per minute under the isomerization conditions described.

Transfructosylation

This term as used herein refers to the transfer of a fructosyl moiety from donor, e.g., sucrose, to an acceptor, e.g., polysaccharide.

Fructosyl Transferase Enzyme

As used herein this term refers to any enzyme that catalyzes transfructosylation and includes the enzyme preparation derived from *Pullularia pullulans* ATCC 9348 (synonomous with *Aureobasidium pullulans*).

Fructosyl Transferase Unit

As used herein, one fructosyl transferase unit is defined as the amount of enzyme activity required to produce one micromole of reducing sugar, calculated as glucose, per minute under the following conditions: (a) pH 5.5, (b) temperature 55° C., and (c) substrate concentration at 60 g food grade sucrose per 100 ml of an aqueous reaction mixture.

Reducing sugar determinations (calculated as glucose) are carried out using a "Technicon Autoanalyzer II" (Technicon, Inc., Tarrytown, New York). Analysis is carried out by a conventional alkaline ferricyanide method, *Analytical Biochemistry* 45, No. 2, pp. 517–524 (1972), adapted for use in the "Autoanalyzer II". Unless otherwise designated, enzyme activity determinations are performed by continual monitoring of a reaction mixture consisting of the following compositon:

- 7.5 ml of 80% (w/v) aqueous food grade sucrose solution
- 2.3 ml 0.1 M citrate buffer pH 5.5
- 0.2 ml enzyme sample containing that amount of fructosyl transferase enzyme which will produce from 5–25 micrograms of reducing sugar (calculated as glucose) per minute per ml of reaction mixture

Primary Substrate

The term "primary substrate" as used herein refers to those saccharides in a form suitable for and having a fructosyl moiety available for participation in transfructosylation, as for example aqueous solutions of sucrose.

Secondary Substrate

The term "secondary substrate" as used herein is the reaction product resulting from subjecting the primary substrate to the action of a fructosyl transferase enzyme preparation, as defined herein.

Immobilized Enzyme

Techniques are now known in the art to "immobilize" or "insolubilize" various enzymes, including isomerase enzymes, by physically or chemically coupling them to essentially insoluble, inert carrier materials, thus facilitating their use in flow-through reactors. As used herein, therefore, the term "immobilized enzyme" means an enzyme which is physically or chemically affixed to an insoluble carrier material. When the immobilized enzyme is contacted with a liquid in which it is normally soluble, the enzyme remains attached to the carrier.

Various materials have been used for the carrier. For instance, enzymes have been bonded to organic materials, such as various cellulose derivatives, polyaminopolystyrene beads, and the like, and various inorganic materials such as porous glass and silica xerogels. Methods for absorbing various enzymes to siliceous materials can be found in U.S. Pat. No. 3,556,945, and methods for chemically coupling enzymes to inorganic carriers are found in U.S. Pat. No. 3,519,538. In the context of this particular invention, the carrier can also be cells of the microorganism which produced the enzyme.

Preferred in the present invention as carriers for immobilized isomerase and fructosyl transferase are porous inorganic materials, and particularly, alkali-resistant ceramic materials. Such preferred porous ceramic carrier materials for isomerase are described in U.S. Pat. Nos. 3,850,751 and 3,868,304, and U.S. Ser. No. 507,209 filed Sept. 18, 1974.

The immobilized fructosyl transferase or isomerase enzyme, e.g., as described in the aforesaid U.S. Pat. Nos. 3,850,751 or 3,868,304 patents and application, are especially advantageously employed in a continuous process where the primary or secondary substrate, as the case may be, is contacted with the immobilized enzyme in a flow-through reactor.

For the process of the present invention, the flow-through reactor is preferably a deep fixed bed reactor such as a column having an L/D (length to diameter) ratio of at least 2:1, preferably at least 3:1. However, columns of other dimensions as well as other flow-through reactors such as shallow fixed bed reactors, fluidized bed reactors, moving bed reactors and the like can also be used.

After a period of time during which the substrate is continuously passed through a bed of immobilized enzyme in a flow-through-reactor, the immobilized enzyme loses activity and the reactor must be discharged and reloaded with fresh immobilized enzyme for another cycle. It is, of course, advantageous for the reactor cycle between recharging to be as long as possible. Also for the process to be economically viable the inert carrier must be regenerated and reused. This can be done, for example, with the preferred ceramic carriers above noted, by subjecting the carrier containing spent immobilized enzyme to pyrolysis, e.g., at 1000°–1300° F. for 2 to 20 hours, and subsequently absorbing fresh enzyme on the regenerated carrier in a manner described in U.S. Pat. No. 3,965,035, the disclosure of which is incorporated herein by reference.

Parts and Percentages

In this application all parts are by weight and all percentages are weight by volume (w/v) unless expressly stated to be otherwise.

High Pressure Liquid Chromatographic Assay

This term as used herein defines the procedure whereby the syrups of the invention are analyzed using high pressure liquid chromatography in accordance with the following technique. Components are chromatographed by elution with water from a cation exchange resin in the calcium form. Eluted components are detected by means of a differential refractometer. Non-dextrose carbohydrates are quantitated using an electronic integrator, and dextrose is obtained by difference. The general procedure is that given in "Analysis of Carbohydrate Mixtures by Liquid Chromatography", *Am. Soc. Brew. Chem. Proc.*, 1973, pp. 43–46. The resin used is "Aminex Q" 15-5 in the calcium form, Bio-Rad Laboratories, Richmond, California.

SUMMARY OF INVENTION

In accordance with the invention, there is provided a process for the production of syrups which comprises subjecting a primary substrate, e.g., sucrose, to the action of a fructosyl transferase enzyme preparation capable of converting the sucrose to a product comprising a monosaccharide fraction containing a major amount of glucose and a minor amount of fructose, and polysaccharides containing at least 66% (by weight) fructosyl moieties. Such product comprises a secondary substrate of this invention. These polysaccharides of the secondary substrate include all fructose-containing polymers (other than sucrose) having two or more monosaccharide moieties. These polymers may be further characterized as including polysaccharides containing fructosyl moieties linked by (2—1)-beta linkages. As described hereinafter, the polysaccharides resultant from given conditions of transfructosylation may lie predominantly within a predeterminable range. Thus, for example, secondary substrate may be produced in which most (e.g., at least 60% by mole ratio) of the polysaccharides are oligomers having from 2 to 10 (i.e., $DP_{2-10}$), more normally 3 to 6 (i.e., $DP_{3-6}$) monosaccharide moieties. Thereafter, said glucose is isomerized (via the action of isomerase enzyme) to fructose in the presence of said polysaccharides, followed by hydrolysis of said polysaccharides in the absence of active isomerase enzyme. The hydrolysis can be carried out enzymatically using invertase or by acid hydrolysis under mild conditions.

In a further embodiment of the invention, the polysaccharides can be separated from said glucose and said fructose, and thereafter, hydrolyzed, as previously described, to produce an ultra-high fructose syrup, e.g., having a fructose content of greater than 66% by weight and preferably greater than 90% by weight, directly from the secondary substrate of this invention without the necessity of isomerization of the dextrose in said substrate. Such separation can conveniently be carried out by conventional physical separation techniques based on molecular size, as for example, conventional membrane technology, (e.g., ultrafiltration, dialysis), solvent precipitation, carbon adsorption and the like. Exemplary of such membrane technology are U.S. Pat. Nos. 3,173,867; Re 26097; 3,541,006; and 3,691,068.

A preferred embodiment is a process for the production of high fructose syrups which comprises subjecting sucrose to the action of a fructosyl transferase enzyme preparation for example that derived from *Pullularia pullulans* such as NRRL 3937; ATCC 9348; ATCC 12535; NRRL 1673; NRRL Y 2311; NRRL YB 3892; ATCC 15223; and NRRL YB 3861. The resulting product, or secondary substrate, is subjected to the action of isomerase enzyme. Thereafter the isomerized product is hydrolyzed in the absence of active isomerase enzyme.

The secondary substrate produced in accordance with the process of this invention is believed to be novel. This substrate is uniquely suitable for isomerization and subsequent hydrolysis to provide a syrup containing greater than 55% fructose, and is produced by subjecting sucrose to the action of a fructosyl transferase enzyme preparation. Therefore another embodiment of this invention are substrates suitable for enzymatic isomerization and subsequent hydrolysis to syrups containing greater than 55% fructose syrup, comprising (1) from about 20% to about 60% by weight monosaccharides, containing a major amount of glucose and a minor amount of fructose, and (2) from about 70% to about 40% polysaccharides containing greater than 66% by weight fructosyl moieties.

Especially preferred are secondary substrates derived from sucrose by transfructosylation in the presence of an effective amount of a fructosyl transferase enzyme preparation derived from a strain of *Pullularia pullulans* ATCC 9348, at a temperature ranging from about 25° C. to about 65° C., and preferably from about 50° C. to about 60° C., and at a pH ranging from about 4.5 to about 6.5, and preferably about 5.4 to about 5.6. The starting sucrose concentrations employed can range as low as 10 g per 100 ml water. However, it is preferred to employ as high a dry substance concentration as possible, preferably ranging from about 30 g to about 60 g per 100 ml (for maximum reaction rate), up to the saturation point of sucrose (and higher, as described more fully hereinafter).

A minimum of 0.5 unit of fructosyl transferase per gram of sucrose can be employed to produce the novel substrate of this invention. Generally, the amount of enzyme used will not exceed 50 units per gram of sucrose because of economic considerations. Especially preferred to obtain the desired secondary substrate in a commercially acceptable time, and within the above described processing parameters, is a range of from about 2 to about 30 units per gram of sucrose.

The foregoing and other embodiments of this invention are described more fully hereinafter.

DETAILED DESCRIPTION OF THE INVENTION

The procedure for production of the novel fructosyl transferase of the invention can utilize conventional fermentation techniques, e.g. see U.S. Pat. Nos. 3,565,756; 3,806,419; 3,535,123; S. Ueda et al., *Applied Microbiology*, 11, 211–215 (1963). Preferably certain novel separation or purification features, which shall be described in more detail hereinafter, are utilized. The following example is a typical fermentation procedure for production of the enzyme from *Pullularia pullulans* ATCC 9348.

EXAMPLE 1

Production of Fructosyl Transferase Enzyme Preparation—Celite Carrier

A. The Fermentation Procedure Used to Produce the Enzyme

The medium used for inoculum development and fermentation to produce the enzyme is as follows:
0.5% Dibasic Potassium Phosphate
0.1% Sodium Chloride
0.02% Magnesium Sulfate-Heptahydrate
0.06% Diammonium Sulfate
0.3% Yeast Extract (Difco Laboratories)
7.5% Sucrose (Food Grade)
pH of medium adjusted to 6.8

The seed flasks, 500 ml Erlenmeyers containing 100 ml of sterile medium, are inoculated from a slant culture of the black yeast, *Pullularia pullulans*. The particular strain of the yeast employed is designated in the catalogue of the American Type Culture Collection (Rockville, Md.) as ATCC 9348. The seed flasks, after development on a reciprocal shaker for 48 hours at 32° C., are used to inoculate one liter Erlenmeyer fermentation flasks, each containing 200 ml of the previously defined medium. The inoculum concentration used is 0.5% w/v. The fermentation is conducted on a reciprocal shaker at 32° C. for 7 days.

B. Recovery of the Enzyme from the Fermentation Broth

The fermentation broths from forty 1-liter shaker flasks are pooled and the flasks are rinsed with water which is also added to the pooled broth. The final volume of the broth after dilution is 12 liters. The original volume of broth is approximately 8 liters. The 12 liters of fermentation broth are run through a Sharples continuous centrifuge to remove the yeast cells and cellular debris. The supernatant, which is a black viscous solution, is then dosed with calcium chloride to a 0.5% w/v concentration and the pH of the resulting solution is adjusted to 7.0 with sodium hydroxide. A second pass is then made through the Sharples centrifuge to produce a viscous supernatant which is low in color. The pH of the decolorized supernatant is adjusted to 5.5 with hydrochloric acid, followed by dosing with 1000 units (as defined in U.S. Pat. No. 3,806,419) of pullulanase. The resultant broth is preserved with toluene (added to saturation) and the pullulanase is allowed to react at ambient temperature overnight. After digestion with pullulanase overnight, a 1% concentration of Grefco #503 Celite (Johns-Manville Products Corporation, Lompoc, Calif.) is slurried in the broth followed by the addition of 2 volumes (24 liters) of acetone. A precipitate forms and is collected by filtration, and the filter cake washed with acetone and dried at ambient temperature. The collected filter cake contains the insolubilized fructosyl transferase enzyme.

In Example 1 it should be noted that the addition of calcium chloride to the fermentation broth, with adjustment of the broth pH, results in the removal of the black pigment and the acidic polysaccharides present. [For discussion of these acidic polysaccharides see Acta. Chem. Scand. 16, 615–622 (1962).] The final enzyme product is thereby rendered in the form of a relatively pure, colorless preparation. This refining procedure constitutes a preferred embodiment of this invention and permits simple refining procedures, i.e. centrifugation, filtration or precipitation, to obtain the final product. Thus, in accordance with this embodiment there is provided a process for separating acidic polysaccharides and black pigment by-products from final fermentation broths of the black yeast, *Pullularia pullulans*. This method renders a final enzyme preparation free of undesirable pigment and acidic polysaccharide by-products, which are formed during the fermentation process. These by-products, unless removed, co-precipitate with the enzyme upon solvent addition to the fermentation broth.

As a further refinement for recovering purified enzyme preparations of this invention, it is desireable to remove the pullulan polysaccharide inherently present in the fermentation broth because it too will co-precipitate with the fructosyl transferase enzyme upon solvent addition to the fermentation broth. Therefore, the supernatant obtained from the calcium chloride treatment and pH adjustment can be further treated with the well-known hydrolyzing enzyme, pullulanase. Pullulanase enzyme randomly hydrolyzes the pullulan to produce a lower molecular weight polymer, thus avoiding coprecipitation and consequent contamination of the fructosyl transferase enzyme preparation during the solvent (e.g. acetone, alcohol and the like) treatment. The purification of the desired fructosyl transferase enzyme in this manner constitutes another novel embodiment of this invention.

The fructosyl transferase enzyme preparations of this invention can be employed without the removal of the pullulan. Thus, this invention can be practiced without hydrolysis of the pullulan by pullulanase, in which case pullulan serves as a carrier for the fructosyl transferase enzyme. The following example demonstrates the use of pullulan as a carrier.

EXAMPLE 2

Production of Secondary Substrate Using Fructosyl Transferase Enzyme On Pullulan Carrier A 20% sucrose solution buffered with 0.05 M citrate buffer pH 5.5 is dosed with a 1% concentration of dry pullulan produced in accordance with the procedure of Example 1, except that the pullulan is not hydrolyzed with pullulanase and, therefore, serves as a carrier and no Celite is employed. Fructosyl transferase activity is 677 units/gram of pullulan. The reaction is carried out at ambient temperature until the mixture becomes hazy. A sample of this material is analyzed by high pressure liquid chromatography with the following results:

| SACCHARIDE DISTRIBUTION BY HPLC ANALYSIS | | | | |
|---|---|---|---|---|
| Fructose | Dextrose | $DP_2$ | $DP_3$ | $DP_{4+}$ |
| 6.9 | 40.6 | 6.2 | 11.1 | 35.2 |

The following examples further characterize the enzyme produced in Example 1.

EXAMPLE 3

Products of Enzymatic Action and Enzyme Thermal Stability

To reaction bottles, equipped with screw-caps, are added 60 g of food grade sucrose and a fructosyl transferase enzyme preparation. The enzyme preparation is obtained from the enzyme product in Example 1 by dispersing suitable aliquots of the solid Celite-enzyme product into measured amounts of water to produce a suitable concentration of an enzyme solution. The Celite is then removed by filtration. The filtrate is used for dosing the reaction mixture at 10, 20 and 30 units of enzyme per gram of sucrose substrate. These mixtures are then each diluted to a final volume of 100 ml with water. Conversions are carried out for 66 hours at pH 5.5 and 55° C. or 60° C., respectively. Samples are taken at 24, 43 and 66 hours for reducing sugar determinations to ascertain the presence of enzymatic activity. After reducing sugar determinations are run on the samples, the remaining reaction mixtures are frozen to stop the enzymatic action and samples submitted for determination of carbohydrate composition by high pressure liquid chromatography. The following results were obtained:

| | | Reducing Sugar Assays[1] | | | | |
|---|---|---|---|---|---|---|
| TEMP. C. | UNITS ENZYME[2] | REDUCING SUGAR mg/ml. 24 HOURS | pH | REDUCING SUGAR mg/ml. 43-HOURS | pH | REDUCING SUGAR mg/ml. 66-HOURS |
| 55° | 0 | — | 5.80 | — | 5.80 | — |
| | 10 | 191 | 5.40 | 231 | 5.25 | 268 |
| | 20 | 192 | 5.40 | 270 | 5.25 | 301 |
| | 30 | 246 | 5.35 | 334 | 5.15 | 390 |
| 60° | 0 | .7 | 5.75 | 1.5 | 5.80 | 2.1 |
| | 10 | 200 | 5.10 | 243 | 4.70 | 270 |
| | 20 | 219 | 5.15 | 288 | 4.90 | 346 |
| | 30 | 282 | 5.20 | 360 | 4.95 | 420 |

[1]Method used set forth under definition of fructosyl transferase unit.
[2]Units enzyme per gram of sucrose.

| CARBOHYDRATE COMPOSITION BY HPLC ANALYSIS | | | | | | |
|---|---|---|---|---|---|---|
| Enzyme Dose unit/per g. sucrose | Reaction Time Hours | Dextrose % | Levulose % | $DP_2$ (%) | $DP_3$ (%) | $DP_4^+$ (%) |
| Reaction Temperature 55° C. | | | | | | |
| 10 | 24 | 31.7 | 2.3 | 10.0 | 25.0 | 31.0 |
| | 43 | 34.5 | 3.2 | 9.4 | 17.9 | 35.0 |
| | 66 | 36.7 | 3.9 | 8.6 | 15.0 | 35.8 |
| 20 | 24 | 33.9 | 2.8 | 8.8 | 19.7 | 34.8 |
| | 43 | 37.4 | 4.2 | 7.9 | 12.1 | 38.4 |
| | 66 | 40.5 | 4.9 | 7.4 | 10.8 | 36.4 |
| 30 | 24 | 37.4 | 4.0 | 7.1 | 12.5 | 39.0 |
| | 43 | 41.8 | 5.9 | 6.8 | 11.4 | 34.1 |
| | 66 | 46.1 | 7.5 | 7.0 | 11.5 | 27.9 |
| Reaction Temperature 60° C. | | | | | | |
| 10 | 24 | 32.2 | 2.8 | 6.1 | 24.3 | 30.6 |
| | 43 | 35.0 | 4.0 | 9.8 | 18.2 | 33.0 |
| | 66 | 36.7 | 5.4 | 9.4 | 16.0 | 32.5 |
| 20 | 24 | 35.5 | 3.8 | 8.4 | 17.1 | 35.2 |
| | 43 | 38.4 | 5.0 | 8.0 | 12.3 | 36.3 |
| | 66 | 41.3 | 6.6 | 7.9 | 11.1 | 33.1 |
| 30 | 24 | 39.0 | 5.5 | 7.1 | 12.1 | 36.3 |
| | 43 | 43.7 | 7.1 | 7.3 | 11.0 | 30.9 |
| | 66 | 47.8 | 9.2 | 7.4 | 11.1 | 24.5 |

Example 3 demonstrates the thermal stability in the presence of substrate of the enzyme at 55° C. and 60° C. throughout a 66 hour period at a pH of 5.5, thus demonstrating the commercial potential of the enzyme. Moreover, the secondary substrate produced by enzymatic conversion of sucrose with the novel fructosyl transferase preparation of this invention is demonstrated by the carbohydrate analysis to be a potentially valuable product suitable for the production of high fructose syrups from sucrose, because the predominant constituents are shown to be dextrose and polymers which upon subsequent hydrolysis yield fructose as the predominant monosaccharide. This example also demonstrates that the novel enzyme of the invention is effective at 60% (w/v) sucrose concentration. Also demonstrated is the functionality of the enzyme in the presence of high glucose concentrations.

EXAMPLE 4

Effect of Temperature on Enzyme Activity

The effect of temperature on the reaction rate of fructosyl transferase enzyme is determined using the "Technicon Autoanalyzer II" as follows:

The reaction mixture consists of 7.5 ml of 80% (w/v) sucrose solution, 2.3 ml of a 0.1 M citrate buffer at a pH of 5.5, and 0.2 ml of a 2% w/v pullulan enzyme solution (enzyme preparation of Example II). Final sucrose concentration is 60% (w/v). The samples are held at the following temperatures and assayed for 10 minutes on the "Technicon Autoanalyzer II." Results demonstrate that at 40° C., enzymatic rate of reaction is 1.89 times that at 30° C.; at 50° C., 1.29 times greater than at 40° C., and at 60° C., 1.48 times greater than at 50° C. This demonstrated an increasing reaction rate with increasing temperature.

EXAMPLE 5

Demonstration Of The Michaelis-Menten Constant ($K_m$) Of The Fructosyl Transferase Enzyme The $K_m$ of an enzyme denotes the substrate concentration at which the rate of product formation is at one-half of the $V_{max}$. The following procedure was used to obtain the $K_m$ of the fructosyl transferase enzyme.

Using a 90% w/v sucrose stock solution adjusted to pH 5.5 with 0.1 M citrate buffer, the proper concentrations of sucrose in 9.8 ml aliquots are prepared to give: 5, 10, 30, 40, 50, 60 and 70% concentrations of sucrose at a final volume of 10 ml. An enzyme solution at 0.2 ml containing 1.1 unit of fructosyl transferase enzyme is added to the attemperated samples. Then the samples are immediately assayed at 55° C. on the "Technicon Autoanalyzer II" as previously described (see fructosyl transferase unit). A glucose standard (calibrated in µg/ml) is included as a control.

Following is the rate of glucose formation expressed as µg/ml/minute at the various substrate concentrations using a constant dose (1.1 unit) of the fructosyl transferase enzyme preparation of Example 1.

| % SUBSTRATE | µg/ml/min | µg/ml/min[a] |
|---|---|---|
| 5 | 8.0 | 8.0 |
| 10 | 11.8 | 11.6 |
| 20 | 15.7 | 15.2 |
| 30 | 18.0 | 17.6 |
| 40 | 18.6 | 18.2 |
| 50 | 19.2 | 17.2 |
| 60 | 17.8 | 18.2 |
| 70 | 15.6 | — |

[a]Rerun next day from a 60% sucrose stock solution

The $K_m$ is 0.27 molar sucrose concentration. Maximum reaction velocity occurred at a substrate concentration of 1.374 molar sucrose, at pH 5.5 and 55° C.

EXAMPLE 6

The Preparation and Isomerization of Secondary Substrate From Sucrose

A. Production of Secondary Substrate

Food Grade Sucrose, 600 g, is dissolved in water to a volume of 800 ml. The pH of this solution is adjusted to 5.5 with dilute hydrochloric acid. A dry Celite-enzyme preparation, 11 g, with an activity of 550 units/g, prepared as in Example 1, is slurried in 100 ml of water. The slurry is filtered under vacuum onto Whatman No. 1 filter paper in a Buchner funnel. The filter cake is washed with an additional 100 ml of water. The 200 ml of filtrate is then added to the sucrose solution, which is in a 0.5 gallon bottle equipped with screw cap. The bottle is then placed in a 58° C. water bath and the reaction is allowed to continue for 20 hours after which time a sample of the reaction product is assayed by high pressure liquid chromatography for determination of carbohydrate composition with the following results:

| Carbohydrate Composition | |
|---|---|
| Fructose | 2.4% |
| Dextrose | 32.8% |
| DP$_2$ | 10.6% |
| DP$_3$ | 22.9% |
| DP$_{4+}$ | 31.3% |

Magnesium chloride is added to the remaining reaction product (i.e., secondary substrate) to a concentration of 5 millimolar, and the pH is adjusted to 8.4 with dilute sodium hydroxide.

B. Continuous Isomerization of Secondary Substrate

Glucose isomerase derived from *Streptomyces olivochromogenes* ATCC 27,715 (See U.S. Pat. No. Re: 29,152) is immobilized on porous alumina (a controlled pore carrier produced by Corning Glass Co., Corning, New York, e.g., see U.S. Pat. No. 3,992,329) as follows:

1. Carrier is washed twice with water;
2. The carrier is incubated with 0.1 M sodium citrate for 1 hour with agitation;
3. The sodium citrate is washed from the carrier until conductivity of the wash solution is 1000 micromhos;
4. The carrier is incubated with 0.05 M magnesium chloride for one hour and the magnesium chloride solution is decanted;
5. A volume of 0.05 M magnesium chloride is then added to provide for a final enzyme concentration of 400 units/ml.
6. The isomerase enzyme concentrate is added to the carrier at a level of 14 million units per cubic foot;
7. The carrier and enzyme are contacted for 22-24 hours and then unbound enzyme is washed from the carrier with distilled water;

A jacketed glass column (3 cm × 18 cm), equipped with a pump connected to a feed supply reservoir, is then loaded with the immobilized enzyme thus prepared. The bed volume of the column after loading is 45 ml. The column is operated at 60° C. for all isomerizations. The loaded column is started on a dextrose syrup (50% w/w concentration) with 5 millimolar of magnesium chloride and adjusted to pH 8.4 to demonstrate that the column is active. The column flow rate is adjusted to 292 ml/hr. The column is then drained to bed level. The introduction of the secondary substrate is conducted manually until 20 ml of effluent are collected and then the flow-rate for the secondary substrate is adjusted to 292 ml/hr. The first 100 ml. of syrup collected is discarded to allow for change of substrate. The remaining secondary substrate (about 850 ml) is then put through the column. After one hour the flow rate increases to 570 ml/hr. The flow rate is adjusted and maintained at 300 ml/hr. to the end of the run. After completion of the run with secondary substrate the column is switched back to dextrose to demonstrate that isomerase activity remains. The following table compares the high pressure liquid chromatography analyses of the starting secondary substrate and final product from the isomerization column:

| | Secondary Substrate (A) | Final Product (B) |
|---|---|---|
| Fructose | 2.4 | 15.7 |
| Dextrose | 32.8 | 18.9 |
| DP$_2$ | 10.6 | 11.0 |
| DP$_3$ | 22.9 | 22.9 |
| DP$_{4+}$ | 31.3 | 31.5 |

These results indicate that 42.38% of the free dextrose in the secondary substrate is isomerized in the column to fructose. Also the fructose polymers present in the secondary substrate did not appear to be affected or to affect the isomerization of dextrose to fructose. It is noteworthy that the total monosaccharide distribution consists of about 45% fructose and 55% dextrose.

In the following example two approaches are employed to cleave the polysaccharides present in the secondary substrate and also the isomerization product therefrom. One approach is enzymatic and the other utilizes a mild acid hydrolysis.

EXAMPLE 7

Preparation of High Fructose Syrup by Hydrolysis

A. Enzymatic Hydrolysis 100 ml of product B from Example 6 is dosed with 10 mg of a purified invertase derived from *Candida utilis*. This mixture (preserved with toluene) is allowed to react overnight at ambient temperature after which a sample is withdrawn and analyzed by high pressure liquid chromatography. The remaining Product B is allowed to continue to react for an additional 6 days and then a second sample is assayed by the same procedure with the following results:

|  | Starting Material (Product B) | After Invertase Action | After Additional Six Days |
|---|---|---|---|
| Fructose | 15.7% | 41.9% | 62.4% |
| Dextrose | 18.9% | 29.4% | 36.2% |
| $DP_2$ | 11.0% | 1.9% | 0 |
| $DP_3$ | 22.9% | 12.9% | 0.5% |
| $DP_{4+}$ | 31.5% | 13.9% | 0.9% |

The invertase employed is an enzyme preparation manufactured by Siekagaku Kogyo Co., Ltd., Tokyo, Japan, having an activity 123 units/mg. where 1 unit of invertase catalyses the cleavage of sucrose to form 1 micromole of glucose and 1 micromole of fructose per minute under specified conditions.

B. Acid Hydrolysis of Product B

Acid hydrolysis of a sample from Product B of Example 6 was carried out by addition of sulfuric acid to a concentration of 0.05 N and heating to 75°–80° C. Samples are taken, after one and two hours of hydrolysis, and analyzed by high pressure liquid chromatography. The results are as follows:

|  | Starting Material (Product B) | 1 Hour | 2 Hours |
|---|---|---|---|
| Fructose | 15.7 | 60.3 | 59.1 |
| Dextrose | 18.9 | 38.7 | 37.9 |
| $DP_2$ | 11.0 | 1.9 | 2.6 |
| $DP_3$ | 22.9 | 0.4 | 0.3 |
| $DP_{4+}$ | 31.5 | 0 | 0.2 |

The above results in Step A show a predominant increase in fructose and a lesser increase in glucose yield occurred with a corresponding drop in the $DP_2$, $DP_3$, and $DP_{4+}$ fractions, thus demonstrating the presence of a fructose polymer.

The results from acid hydrolysis in Step B are in accord with those obtained in Step A, thus also demonstrating cleavage of fructose polymers.

The foregoing discussion is directed to transfructosylation using a primary substrate wherein the dry substance content of starting sucrose does not exceed the saturation point under given reaction conditions. The following example demonstrates the use of a primary substrate having an initial sucrose concentration in excess of saturation and which, when subjected to the action of the fructosyl transferase enzyme, results in a product containing increased levels of $DP_3$ material (i.e. fructosyl-sucrose) and a decreased concentration of $DP_{4+}$ products. Also exhibited is an increase in the dry substance concentration (w/w) of the secondary substrate over the dry substance concentration obtained in the absence of the action of the fructosyl transferase enzyme. Moreover, it is demonstrated that, when the dry substance concentration of the primary substrate increases, the degree of polymerization of the fructose polymer in the secondary substrate decreases and the $DP_{4+}$ material is present in minor accounts.

This is in marked contrast to the results obtained in the previous examples using sucrose substrates at less than saturation. In those examples the $DP_{4+}$ material is the primary product.

EXAMPLE 8

Preparation of Secondary Substrate from Sucrose Slurries in Excess of Saturation Food Grade Sucrose in 200 g aliquots is placed in one pint jars with screw-cap lids. As a control, 50 ml of water is added to one jar and the other each receive 50 ml water containing increasing amounts of fructosyl transferase enzyme-Celite preparation (produced in accordance with Example 1), as shown in the following table. Each is capped and placed in a shaking water bath set at 54°–55° C. The flasks are shaken for 24 hours with occasional manual mixing. A sample of supernatant is withdrawn from each bottle and placed in a screw-cap test tube in a boiling water bath to inactivate the enzyme. These samples are then analyzed by high pressure liquid chromatography and supernatant dry substance determinations are made (K. Fischer method) with the following results:

| Bottle No. | Sucrose(g) | Enzyme[1] Units | Dry Substance in Supernatant (w/w) | Composition of Carbohydrates in Solution by HPLC (%) | | | | |
|---|---|---|---|---|---|---|---|---|
|  |  |  |  | Fruc. | Dex. | $DP_2$ | $DP_3$ | $DP_{4+}$ |
| 1 | 200 | 100 | 74.5 | 0.6 | 9.6 | 80.9 | 8.9 | ND[2] |
| 2 | 200 | 200 | 75.6 | 0.7 | 12.7 | 72.2 | 13.7 | 0.7 |
| 3 | 200 | 300 | 76.3 | 1.0 | 14.5 | 66.8 | 16.6 | 1.1 |
| 4 | 200 | 400 | 77.1 | 0.9 | 15.7 | 62.6 | 19.0 | 1.8 |
| 5 | 200 | 500 | 77.7 | 1.1 | 17.3 | 58.5 | 21.0 | 2.1 |
| 6 | 200 | 600 | 78.1 | 1.3 | 18.0 | 56.0 | 21.9 | 2.8 |
| 7 | 200 | 700 | 78.1 | 1.1 | 18.8 | 53.9 | 23.1 | 3.0 |
| 8 | 200 | 800 | 80.0 | 1.0 | 19.3 | 52.2 | 24.1 | 3.4 |
| 9 | 200 | 900 | 79.0 | 1.3 | 19.9 | 50.0 | 25.0 | 3.7 |
| 10 | 200 | 1000 | 79.6 | 1.3 | 20.6 | 48.6 | 25.4 | 4.1 |
| Control | 200 | None | 72.7 | 0.3 | ND[2] | 99.7 | ND[2] | ND[2] |

[1]Total units of fructosyl transferase enzyme in 50 ml water
[2]ND = none detected It is noteworthy that in the above example, the control crystallized when cooled to ambient temperature (about 25° C.) whereas the enzymatically produced secondary substrates remain in solution and exhibit excellent shelf-life stability without crystallization.

Although Example 8 employs 200 g sucrose per 50 ml of water, i.e. 80% w/w, the dry substance concentration of the sucrose starting material can be increased.

The novel secondary substrate of this embodiment can be used as a highly stable, non-crystallizing syrup in food applications. It also provides a uniquely high dry substance composition, resistant to microbial contamination and color body formation, which can be employed to ship and/or store the sugar at concentrations heretofore not obtainable in a form having the above described properties. Moreover, this novel high dry substance secondary substrate can be subjected to hydrolysis as shown in Example 7 to obtain an invert sugar mixture having a desireable sweetness level. The novel secondary substrate of this embodiment has a dry substance content (w/w) ranging from about 70% to about 82% and contains a monosaccharide fraction consisting essentially of dextrose and polysaccharide polymers, in excess of $DP_2$, consisting predominately of $DP_3$ product. A minor amount (4.1% and below) of $DP_{4+}$ polymers is also present.

Although the transfructosylation step of this invention has been demonstrated in terms of batch unit operations, it will be apparent to those skilled in the art that continuous unit operations can likewise be employed. In carrying out such continuous transfructosylation, the transfructosylase enzyme is conveniently immobilized using the techniques previously discussed under the definition of immobilized enzyme and the continuous processing methodology therein described.

I claim:

1. A process for the production of a product containing greater than 55% fructose consisting essentially of subjecting sucrose to the action of a cell-free fructosyl transferase enzyme derived from *Pullularia pullulans* capable of converting the sucrose to a mixture comprising glucose, fructose, and polysaccharides containing at least 66% by weight of fructosyl moieties wherein the fructosyl moieties are linked by (2-1)-beta linkages, subjecting the mixture to the action of a glucose isomerase enzyme, and hydrolyzing the polysaccharides in the mixture in the absence of active isomerase enzyme.

2. The process of claim 1 wherein said fructosyl transferase enzyme preparation is derived from *Pullularia pullulans* ATCC 9348.

3. The process of claim 1 wherein said isomerizing step is carried out using an immobilized glucose isomerase enzyme.

4. The process of claim 1, wherein said sucrose is at a concentration of at least about 20 percent.

5. A method for producing a high fructose syrup consisting essentially of (1) subjecting sucrose to the action of an effective amount of a cell-free fructosyl transferase enzyme to produce a reaction mixture containing dextrose, fructose and polysaccharides containing at least 66% by weight of fructosyl moieties wherein the fructosyl moieties are linked by (2-1)-beta linkages, (2) isomerizing part of the free dextrose in the reaction mixture to fructose, and (3) hydrolyzing the polysaccharides in the reaction mixture.

6. A method for producing a fructose syrup which comprises subjecting sucrose to the action of an enzyme preparation consisting essentially of fructosyl transferase enzyme derived from *Pullularia pullulans* ATCC 9348 to give a product comprising glucose, a fructose and polysaccharides containing at least 66% by weight of fructosyl moieties wherein the fructosyl moieties are linked by (2-1)-beta linkages, separating said polysaccharides from said glucose and said fructose, and hydrolyzing the polysaccharides thereby produced.

7. A process for producing a novel substrate, suitable for production of a syrup containing greater than 55% fructose, which comprises subjecting an aqueous solution of sucrose at a concentration of at least about 10 grams sucrose per 100 ml of water to the action of an enzyme preparation consisting essentially of fructosyl transferase enzyme derived from *Pullularia pullulans* ATCC 9348 at a temperature of from about 25° C. to about 65° C. and at a pH of from about 4.5 to about 6.5 for a sufficient time to give a product wherein at least 60% by mole ratio of the polysaccharides are oligomers having from 3 to 6 monosaccharide moieties, and then inactivating the enzyme.

* * * * *

UNITED STATES PATENT AND TRADEMARK OFFICE
CERTIFICATE OF CORRECTION

PATENT NO. : 4,276,379
DATED : June 30, 1981
INVENTOR(S) : Robert E. Heady

It is certified that error appears in the above-identified patent and that said Letters Patent are hereby corrected as shown below:

Column 2, line 62, delete "21.714" and insert --21,714--.

Column 3, line 61, delete "synonomous" and insert --synonymous--.

Column 8, line 30, delete "desireable" and insert --desirable--.

Column 14, line 9, delete "accounts" and insert --amounts--.

Column 15, line 1, delete "desireable" and insert --desirable--.

Claim 5, line 4, after "enzyme" insert --derived from Pullularia pullulans--.

Claim 6, line 5, after "glucose," delete --a--.

Signed and Sealed this

Twelfth Day of July 1983

[SEAL]

Attest:

Attesting Officer

GERALD J. MOSSINGHOFF
Commissioner of Patents and Trademarks